US006746431B2

(12) United States Patent
Pfeiffer et al.

(10) Patent No.: US 6,746,431 B2
(45) Date of Patent: Jun. 8, 2004

(54) COMBINED CATHETER SYSTEM FOR IABP AND DETERMINATION OF THERMODILUTION CARDIAC OUTPUT

(75) Inventors: Ulrich J. Pfeiffer, Munich (DE); Steve Allen, Houston, TX (US); Ulf Borg, Wilmington, NC (US)

(73) Assignee: Pulsion Medical Systems AG (DE)

( * ) Notice: Subject to any disclaimer, the term of this patent is extended or adjusted under 35 U.S.C. 154(b) by 336 days.

(21) Appl. No.: 09/834,905

(22) Filed: Apr. 16, 2001

(65) Prior Publication Data

US 2001/0037048 A1 Nov. 1, 2001

Related U.S. Application Data

(62) Division of application No. 09/338,543, filed on Jun. 23, 1999, now Pat. No. 6,231,498.

(51) Int. Cl.[7] .................................................. A61M 5/31
(52) U.S. Cl. ....................... 604/284; 607/18; 604/96.01
(58) Field of Search .............................. 600/16, 17, 18; 604/96.01, 97.01, 284

(56) References Cited

U.S. PATENT DOCUMENTS

| | | | |
|---|---|---|---|
| 3,585,983 A | 6/1971 | Kantrowitz | |
| 3,995,623 A | 12/1976 | Blake et al. | |
| 4,077,394 A | 3/1978 | McCurdy | |
| 4,105,022 A | 8/1978 | Antoshkiw et al. | |
| 4,733,652 A | 3/1988 | Kantrowitz et al. | |
| 4,878,898 A | 11/1989 | Griffin et al. | |
| 5,004,472 A | 4/1991 | Wallace | |
| 5,330,451 A | * 7/1994 | Gabbay | |
| 5,484,385 A | 1/1996 | Rishton | |
| 5,697,906 A | 12/1997 | Ariola et al. | |
| 5,711,754 A | 1/1998 | Miyata et al. | |
| 5,759,175 A | 6/1998 | Ariola et al. | |
| 5,865,721 A | 2/1999 | Andrews et al. | |

OTHER PUBLICATIONS

European Search Report.

* cited by examiner

*Primary Examiner*—Scott M. Getzow
(74) *Attorney, Agent, or Firm*—Nixon Peabody LLP; Donald R. Studebaker

(57) ABSTRACT

An intro-aortic balloon catheter system and method for determining cardiac output with the system including a distal end for insertion into an aorta and a proximal end opposed to the distal end, a balloon portion in proximity to the distal end which repeatedly expands and contracts so as to assist the pumping action of the heart, a catheter tube connected to the balloon portion with the catheter tube having a lumen introducing a pressurized gas into the balloon portion and leading the pressurized gas out from the balloon portion and a temperature sensor attached to the catheter tube and being electrically coupled to a connector at the proximal end of the catheter tube. The method includes inserting the temperature sensor into a lumen of the intra aortic balloon catheter system, advancing the temperature sensor until it projects freely into the aorta, injecting an injectate of a temperature different to that of the temperature of the patient's blood into the central vein of the patient, measuring the blood temperature profile versus time by means of the temperature sensor and calculating cardiac output and optionally the derived variables from the measured temperature profile.

16 Claims, 2 Drawing Sheets

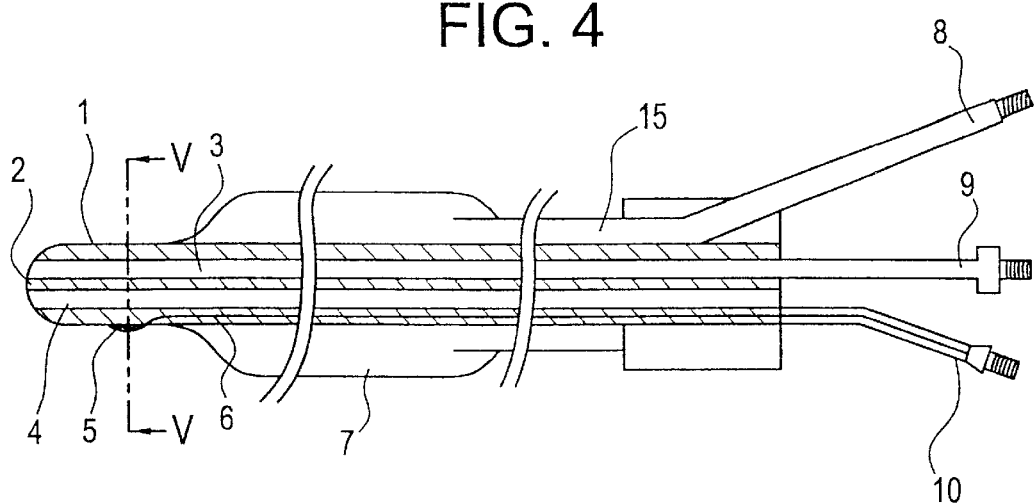
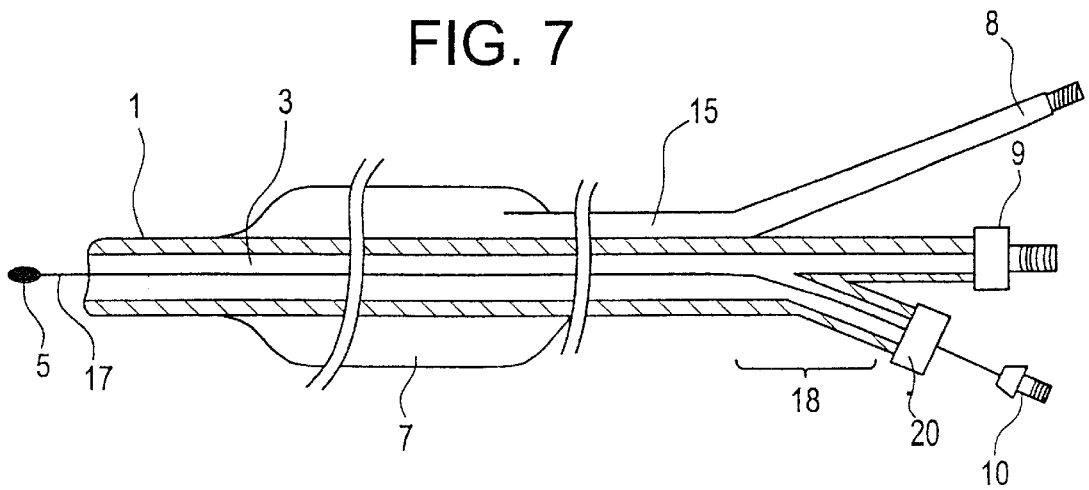

COMBINED CATHETER SYSTEM FOR IABP AND DETERMINATION OF THERMODILUTION CARDIAC OUTPUT

BACKGROUND OF THE INVENTION

1. Field of the Invention

This invention relates to an intra-aortic balloon catheter system.

2. Description of the Related Art

The intra-aortic balloon pump (IABP) is a temporary circulatory assist device for patients with extreme low cardiac output syndrome, e.g. after myocardial ischemia due to coronary heart disease. IABP catheters for aortic counterpulsation have been described in several previous patents (U.S. Pat. Nos. 4,733,652; 5,484,385; 5,697,906; 5,711,754; 5,759,175).

This device, based on the principle of counterpulsation, improves the blood supply of the heart muscle and other organs during cardiogenic shock or open heart surgery for coronary bypass grafting and subsequently decreases the mortality of these patients.

Usually, the IABP catheter is placed in the femoral artery using the guide wire technique: after puncturing the vessel, the guide wire is introduced. This wire is needed to install a percutaneous introducing sheath, i.e. an arterial line with larger inner diameter than the outer diameter of the IABP catheter. At the proximal end, this sheath has an hemostatic valve, which is used for a non traumatic introduction of the IABP catheter, e.g. in the femoral artery.

Distally, a long narrow balloon is attached to the catheter body that is connected to a computer controlled pump system via the proximal end of the catheter. Depending on the clinical requirements the ECG or the femoral pulse triggers the inflation and deflation of the catheter balloon with helium or carbon dioxide gas. The inflation occurs at the end of the systolic phase of the heart beat, i.e. right after closure of the aortic valve, and produces an increased intra-aortic pressure, followed by elevated coronary and systemic blood flow. Exactly before the next systole is about to start, the balloon is deflated to avoid an extensive afterload to the already damaged heart.

The medical indication of the IABP system is life threatening insufficiency of the heart and the circulation. As a consequence, these patients require intensive cardiovascular monitoring to guarantee optimal therapy strategy. One of the most important parameters in this context is the actual performance of the heart, the cardiac output (CO) or cardiac index, respectively.

Determination of CO is routinely performed by pulmonary thermodilution with a right heart catheter (RHC) or—alternatively—by transpulmonary arterial thermodilution: with this technique, no RHC for hemodynamic monitoring is necessary. An arterial line with integrated thermistor is inserted percutanously into the femoral artery with Seldinger technique and connected to a corresponding CO monitor. Via a conventional central venous line a defined amount of normal saline, e.g. 10 ml, with a defined temperature significantly below the blood temperature, at least room temperature, Is injected rapidly. The CO catheter in the femoral artery records changes in the blood temperature caused by the indicator following the same principle as the RHC. Depending on myocardial function, washout of the indicator Is accomplished fast or slow. According to the theory of Stewart and Hamilton, the CO can be calculated by the integral of the indicator dilution curve:

$$CO = \frac{V_i \cdot (T_B - T_i) \cdot K}{\int_0^\infty \Delta T_B \, dt}$$

where: $\Delta T_B$ is the blood temperature change after injection, $V_i$ is the injectate volume, $T_B$ is the blood temperature before injection, $T_i$ is the injectate temperature, K is a correction factor taking into account specific heat and weight of injectate and blood and loss of indicator during injection.

Assessment of cardiac output simultaneously to IABP is usually performed by introducing a RHC.

U.S. Pat. No. 3,995,623 discloses a multipurpose flow directed catheter (right heart catheter). This catheter is flow-directed through the heart of the patient by a balloon on its distal end to pass through the right atrium, right ventricle and into the pulmonary artery. A thermistor proximal to the balloon permits monitoring of blood temperature and thus allows the determination of cardiac output by the thermodilution technique.

Measurement of CO with a RHC however means increased strain and risk for further complications for the critically inpatient. Several studies in the last few years have demonstrated significant incidence of complications in association with the use of the RHC, especially infections and traumatic lesions, or even increased mortality due to the device itself.

Determination of CO by transpulmonary thermodilution in the femoral artery simultaneously to the treatment with the IABP is not advisable. The contralateral femoral artery not used for IABP has to be cannulated for the placement of the CO catheter. Catheters would occupy both femoral arteries and in case of an emergency operation this may be problematic, since the available femoral artery normally is the emergency access for extracorporeal circulation.

SUMMARY OF THE INVENTION

It is therefore an object of the present invention to overcome the deficiencies of the prior art devices by providing an IABP enabling an online measurement of the cardiac output without an additional intravascular access and without interruption of the circulatory assist of the IABP.

A further object of the present invention is to provide a IABP catheter which allows the determination of cardiac output without using a right heart catheter (Swan-Ganz-catheter).

A still further object of the present invention is to provide an IABP catheter which allows the determination of the cardiac output with minimal stress and risk for the critically ill patient.

In accomplishing these and other objectives of the present invention, there Is provided an intra-aortic balloon catheter system comprising a temperature sensor (thermistor). Such a thermistor is comparable with thermistors used in RHC or arterial thermodilution catheters and is suitable for the determination of CO.

Placement of the thermistor in the catheter may vary, however, the tip of the thermistor is constantly in the blood stream to ensure an optimal recording of the change in blood temperature. One possible position for the thermistor is on the outside of the catheter body about 2 cm behind the tip (distal end). In this case it has to be ensured that the thermistor tip is not covered respectively isolated by the material of the catheter body. In this way a heating of the surrounding material and subsequently an indicator loss for the thermistor is avoided. The typical response time of the thermistor is comparable to those in RHCs or arterial thermodilution catheters.

The course of the thermistor wire would preferably be in the inner lumen of the body of the catheter.

Alternatively, the thermistor can be introduced separately after placement of the IABP catheter via the port of the inner lumen: for this possibility, the thermistor wire is equipped with markings or delineations providing information about the depth of the thermistor location within the patient: for optimal measurements the thermistor tip has to overtop the IABP catheter tip about 1 to 2 cm for a proper placement in the free blood stream.

All different technical units of the system are divided in different channels at the proximal end of the catheter: one for the gas pump, one for the arterial blood pressure measurement and the thermistor line with a transpulmonary thermodilution computer. Subsequently, the catheter can be connected to every clinically used commercial monitoring system as long as it is equipped with the necessary algorithm for calculation of transpulmonary cardiac output and derived variables.

Other features, characteristics and advantages of the present invention will become apparent from the following description of the invention, which refers to the accompanying drawings.

BRIEF DESCRIPTION OF THE DRAWINGS

FIG. 4 is a highly enlarged longitudinal section of the complete catheter system (with interruptions).

FIG. 5 is an enlarged cross-sectional view taken along line V—V of FIG. 4

FIG. 6 is a highly enlarged longitudinal section of a further embodiment of the invention.

FIG. 7 is a highly enlarged longitudinal section of a still further embodiment of the invention in which the thermistor probe is inserted via the pressure lumen of the IABP catheter through a Y-piece with valve attached to the proximal end of the pressure lumen.

DETAILED DESCRIPTION OF THE PREFERRED EMBODIMENTS

Figure 1:
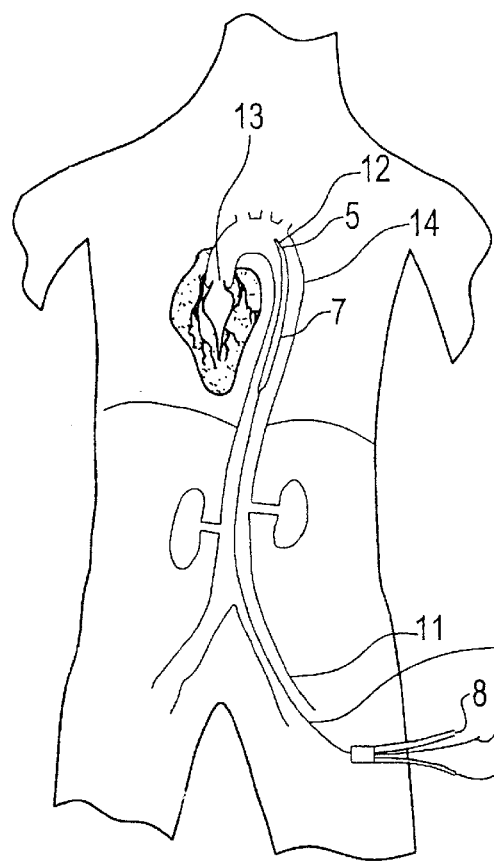
FIG. 1 is a schematic demonstration of the catheter system in situ.

In FIG. 1 the catheter body 1 has been introduced percutaneously into the femoral artery 11 over a guidewire and has been advanced through the vasculature into the aorta 14 until the distal tip 12 of the catheter body 1 is positioned just below the subclavian artery. Once in position a balloon pump (not shown) is connected to connector 8 to operate the balloon 7 synchronously with the patient's heart beat. In particular, the balloon 7 can be inflated and deflated to assist blood circulation especially into the coronar arteries. Inflation of the balloon occurs as the aortic valve 13 is closing and deflation occurs just prior to the onset of systole. At the proximal end of the catheter body there is provided a Luer-Lock connector 9 to connect an inner lumen of the catheter body 1 to a blood pressure monitor (not shown).

Close to the distal tip 12 of the catheter body 1 there is provided a thermistor 5 which permits monitoring of the blood temperature of the blood flowing in the aorta 14. The thermistor is coupled to a wire which is terminated by a thermistor coupler 10 at the proximal end of the catheter body 1.

Figure 2:
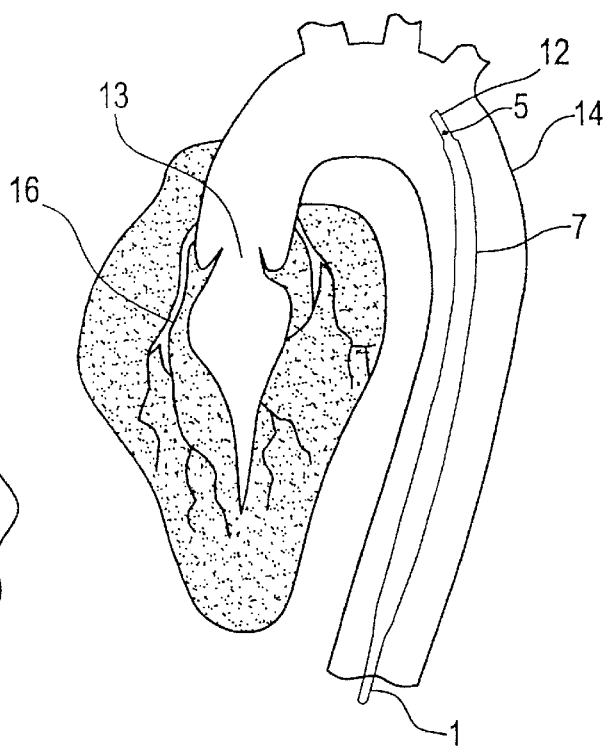
FIG. 2 shows the catheter system in the aorta during systole.
Figure 3:
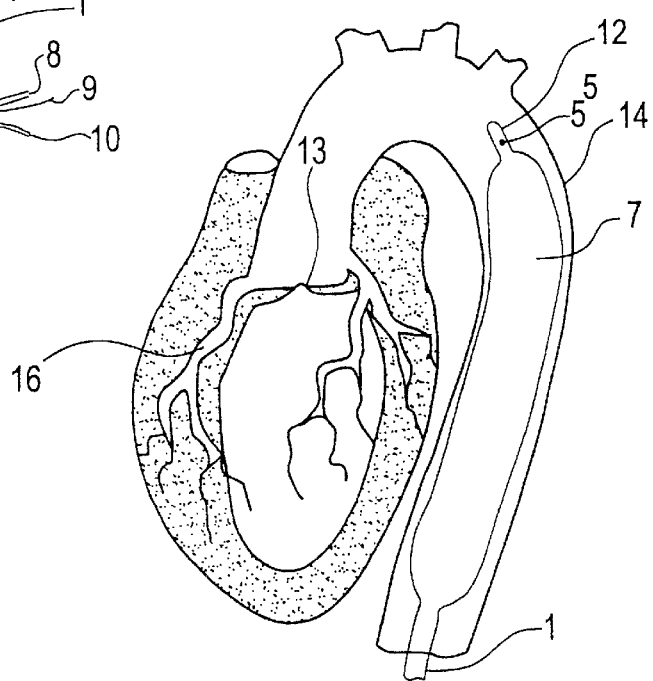
FIG. 3 shows the catheter system in the aorta during diastole.

The pumping operation of the intra-aortic balloon catheter is demonstrated with the aid of FIGS. 2 and 3.

FIG. 2 shows the heart with open aortic valve 13 (systole), the balloon 7 being in its deflated state in order to decrease afterload and not to impede the pumping action of the heart.

FIG. 3 shows the heart during diastole, the aortic valve 13 being closed. The balloon 7 is inflated in order to augment the aortic pressure and to favour blood perfusion especially of the coronar arteries 16.

FIG. 4 is a longitudinal section of the balloon catheter according to the invention. The catheter comprises a catheter body 1 having a first inner lumen 3 and a second inner lumen 4, the two lumina being separated from each other by a partition 2.

An outer lumen 15 is in communication with an inflatable balloon 7. The outer lumen 15 communicates at the proximal end of the catheter body 1 to a connector 8 which is to be coupled to a pump (not shown). The first inner lumen 3 is connected at the proximal end of the catheter body 1 to a Luer-Lock connector 9 which allows coupling to a blood pressure monitor (not shown).

Approximately 2 cm proximal to the catheter tip there is a thermistor 5 attached to the outer surface of the catheter body 1. The thermistor 5 is coupled to a thermistor line 6 which leads to the proximal end of the catheter body 1 where it is terminated by a thermistor coupler 10 which may be coupled to a temperature monitor (not shown). The thermistor line 6 is immersed in the outer wall of the catheter body 1.

As becomes apparent from the cross section of FIG. 5 the thermistor 5 is immersed in the outer wall of the housing of the catheter body 1 in order not to impede advancing of the catheter in the blood vessel but simultaneously allows a good contact to the flowing blood for rapidly determining its temperature.

FIG. 6 shows a further embodiment according to which the thermistor 5 is provided with a stiff wire 17 so that it can be advanced in the second lumen 4 until it projects over the catheter tip for getting into contact with the flowing blood. Markers (not shown) near the proximal end of wire 17 indicate for the doctor when wire 17 has been advanced a sufficient depth into the patient's body to reach the position shown in FIG. 6, where it projects into the free blood stream.

FIG. 7 shows a still further embodiment which has only one inner lumen 3 which is mainly used for arterial blood pressure monitoring, the outer lumen 15 for inflating and deflating the balloon 7 being designed in the same way as the outer lumen 15 of the embodiments of FIGS. 4 and 6. At the proximal end of lumen 3 there is provided a Y-junction 18 having at one of its branches the Luer-Lock connector 9 for connecting to a blood pressure monitor and at the other one of its branches a valve 20 for inserting the thermistor 5 together with the stiff wire 17 which is terminated by a thermistor coupler 10 at its proximal end.

The catheter systems especially explained with reference to FIGS. 5, 6, and 7 above are used as follows: The catheter body 1 is advanced into the aorta of the patient and operated as already previously described with reference to FIGS. 1 and 3. In order to determine the cardiac output an injectate having a significantly lower temperature than the temperature of the patient's blood is injected rapidly into a vein, preferable the central vein or the right atrium of the patient. The temperature profile in response to the injection is monitored with the aid of thermistor 5 and the cardiac output, the global end-diastolic volume, the intrathoracic blood volume, and the extravascular lung water are calculated therefrom according to algorithms well known in the art. The measurement of cardiac output according to the invention does not burden the critically ill patient because the intravenous injection of the cold injectate can be done easily particularly for critically ill patients which have normally a permanent intravenous access for other medical purposes.

What is claimed is:

1. An intra-aortic balloon catheter system having a distal end for inserting into an aorta and a proximal end opposed to said distal end, the system comprising:
   a balloon portion in proximity to said distal end which repeatedly expands and contracts so as to assist pumping action of the heart;
   a catheter tube connected to said balloon portion, the catheter tube having a first lumen for introducing a pressurized gas into and leading the pressurized gas out from said balloon portion, and
   a second lumen, extending in direction of insertion distally to said balloon, for receiving a temperature sensor.

2. The intra-aortic balloon catheter system as set forth in claim 1, further comprising a temperature sensor being connected to a wire having a length greater than said catheter tube so as to project beyond the distal end of said catheter tube.

3. The intra-aortic balloon catheter system as set forth in claim 2, said wire having a marker close to its proximal end indicating when said temperature sensor has reached its position at the distal end of said catheter tube.

4. The intra-aortic balloon catheter system as set forth in claim 1, said catheter tube having a further lumen for monitoring blood pressure.

5. An intra-aortic balloon catheter system having a distal end for inserting into an aorta and a proximal end opposed to said distal end, the system comprising:
   a balloon portion in proximity to said distal end which repeatedly expands and contracts so as to assist pumping action of the heart; and
   a catheter tube connected to said balloon portion, the catheter tube having a first lumen for introducing a pressurized gas into and leading the pressurized gas out from said balloon portion;
   wherein the catheter tube includes a second lumen for receiving a temperature sensor and said second lumen has a Y-junction forming two branches at its proximal end, the two branches of said Y-junction being connected to a blood pressure monitor and a thermistor coupler, respectively.

6. The intra-aortic balloon catheter system as set forth in claim 5, said temperature sensor being connected to a wire having a length greater than said catheter tube so as to project beyond the distal end of said catheter tube.

7. The intra-aortic balloon catheter system as set forth in claim 6, said wire having a marker close to its proximal end indicating when said temperature sensor has reached its position at the distal end of said catheter tube.

8. The intra-aortic balloon catheter system as set forth in claim 5, said catheter tube having a further lumen for monitoring blood pressure.

9. The intra-aortic balloon catheter system as set forth in claim 5, said catheter tube having a further lumen for monitoring blood pressure.

10. An intra-aortic balloon catheter system having a distal end for inserting into an aorta and a proximal end opposed to said distal end, the system comprising:
    a balloon portion in proximity to said distal end which repeatedly expands and contracts so as to assist pumping action of the heart;
    a catheter tube connected to said balloon portion, the catheter tube having a first lumen for introducing a pressurized gas into and leading the pressurized gas out from said balloon portion;
    a temperature sensor, and
    a second lumen for receiving said temperature sensor.

11. The intra-aortic balloon catheter system as set forth in claim 10, said temperature sensor being connected to a wire having a length greater than said catheter tube so as to project beyond the distal end of said catheter tube.

12. The intra-aortic balloon catheter system as set forth in claim 11, said wire having a marker close to its proximal end indicating when said temperature sensor has reached its position at the distal end of said catheter tube.

13. The intra-aortic balloon catheter system as set forth in claim 10, said catheter tube having a further lumen for monitoring blood pressure.

14. An intra-aortic balloon catheter system having a distal end for inserting into an aorta and a proximal end opposed to said distal end, the system comprising:
    a balloon portion in proximity to said distal end which repeatedly expands and contracts so as to assist pumping action of the heart;
    a catheter tube connected to said balloon portion, the catheter tube having a first lumen for introducing a pressurized gas into and leading the pressurized gas out from said balloon portion; and
    a temperature sensor,
    wherein the catheter tube includes second lumen for receiving said temperature sensor and said second lumen has a Y-junction forming two branches at its proximal end, the two branches of said Y-junction being connected to a blood pressure monitor and a thermistor coupler, respectively.

15. The intra-aortic balloon catheter system as set forth in claim 14, said temperature sensor being connected to a wire having a length greater than said catheter tube so as to project beyond the distal end of said catheter tube.

16. The intra-aortic balloon catheter system as set forth in claim 15, said wire having a marker close to its proximal end indicating when said temperature sensor has reached its position at the distal end of said catheter tube.

* * * * *